United States Patent
Anand et al.

(10) Patent No.: US 12,408,877 B2
(45) Date of Patent: Sep. 9, 2025

(54) PERSONALIZED NON-INVASIVE BLOOD GLUCOSE MEASUREMENT DEVICE USING MACHINE LEARNING OR DEEP LEARNING AND METHOD USING THE MEASUREMENT DEVICE

(71) Applicant: Research & Business Foundation Sungkyunkwan University, Suwon-si (KR)

(72) Inventors: Pradeep Kumar Anand, Suwon-si (KR); Dong Ryeol Shin, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 1190 days.

(21) Appl. No.: 16/777,033

(22) Filed: Jan. 30, 2020

(65) Prior Publication Data
US 2020/0367833 A1 Nov. 26, 2020

(30) Foreign Application Priority Data
May 22, 2019 (KR) .................. 10-2019-0060012

(51) Int. Cl.
*A61B 5/00* (2006.01)
*A61B 5/145* (2006.01)
(Continued)

(52) U.S. Cl.
CPC ........ *A61B 5/7275* (2013.01); *A61B 5/14532* (2013.01); *G06N 20/00* (2019.01);
(Continued)

(58) Field of Classification Search
CPC .............. A61B 5/7275; A61B 5/14532; A61B 2560/0228; G06N 20/00; G16H 10/40; G16H 50/50
See application file for complete search history.

(56) References Cited

U.S. PATENT DOCUMENTS

2003/0109998 A1* 6/2003 Lorenz ................. G01N 21/359
702/85
2003/0191377 A1* 10/2003 Robinson ............. A61B 5/1495
600/310
(Continued)

FOREIGN PATENT DOCUMENTS

JP 2005-519683 A 7/2005
JP 2009-039267 A 2/2009
(Continued)

OTHER PUBLICATIONS

Jul. 2024 Subject Matter Eligibility Examples, USPTO (Year: 2024).*
(Continued)

*Primary Examiner* — Christian Jang
(74) *Attorney, Agent, or Firm* — NSIP Law

(57) ABSTRACT

A personalized non-invasive blood glucose measurement method according to the present disclosure includes: (a) collecting blood glucose value data of a patient by a processor unit; (b) determining an acceptable final error E' with the blood glucose value data collected by the processor unit; (c) non-invasively predicting a blood glucose value in accordance with a setting mode by a patient when the final error E' is determined, to measure a blood glucose value, by the processor unit; (d) periodically determining whether the final error E' is calibrated by the processor unit; and (e) when it is not necessary to recalibrate in step (d), non-invasively predicting the blood glucose value in the range of the final error E' determined in step (b) to measure the blood glucose
(Continued)

value, to non-invasively provide an accurate personalized blood glucose value to a patient who needs to invasively measure a blood glucose every day.

8 Claims, 3 Drawing Sheets

(51) Int. Cl.
  *G06N 20/00* (2019.01)
  *G16H 10/40* (2018.01)
  *G16H 50/50* (2018.01)
(52) U.S. Cl.
  CPC ............. *G16H 10/40* (2018.01); *G16H 50/50* (2018.01); *A61B 2560/0228* (2013.01)

(56) References Cited

U.S. PATENT DOCUMENTS

| | | | |
|---|---|---|---|
| 2016/0262707 A1* | 9/2016 | DeVries | A61B 5/1455 |
| 2017/0181671 A1* | 6/2017 | Varsavsky | A61B 5/0537 |
| 2019/0069821 A1* | 3/2019 | Segman | A61B 5/14532 |

FOREIGN PATENT DOCUMENTS

| | | |
|---|---|---|
| KR | 10-2012-0095037 A | 8/2012 |
| KR | 10-2019-0043034 A | 4/2019 |

OTHER PUBLICATIONS

Korean Office Action issued on Sep. 17, 2020 in counterpart Korean Patent Application No. 10-2019-0060012 (7 pages in Korean).

* cited by examiner

[FIG. 1]
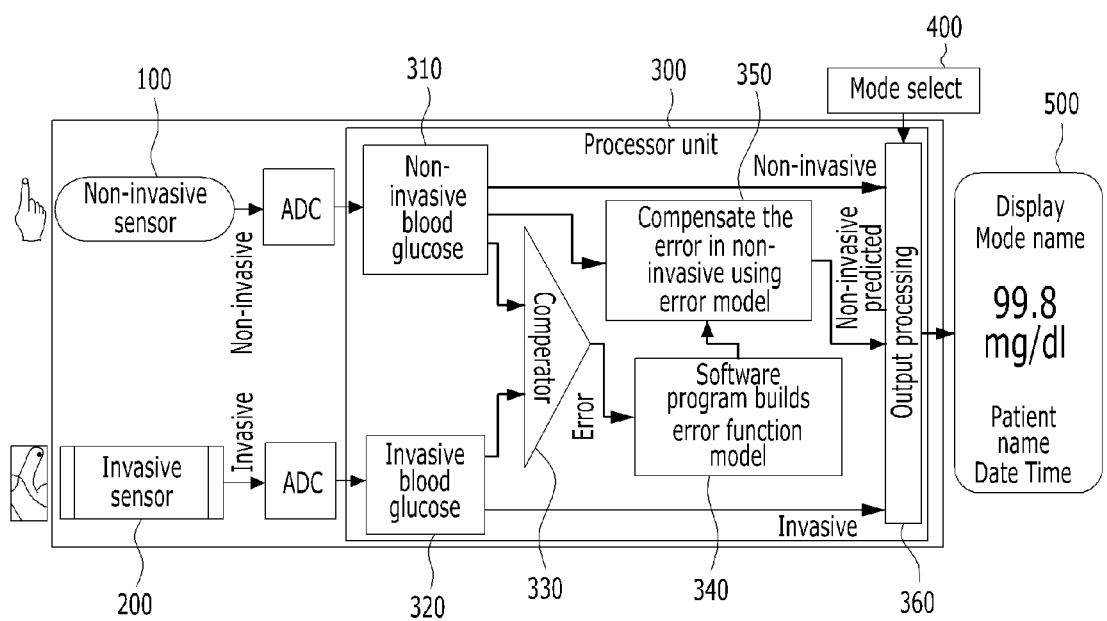

[FIG. 2]
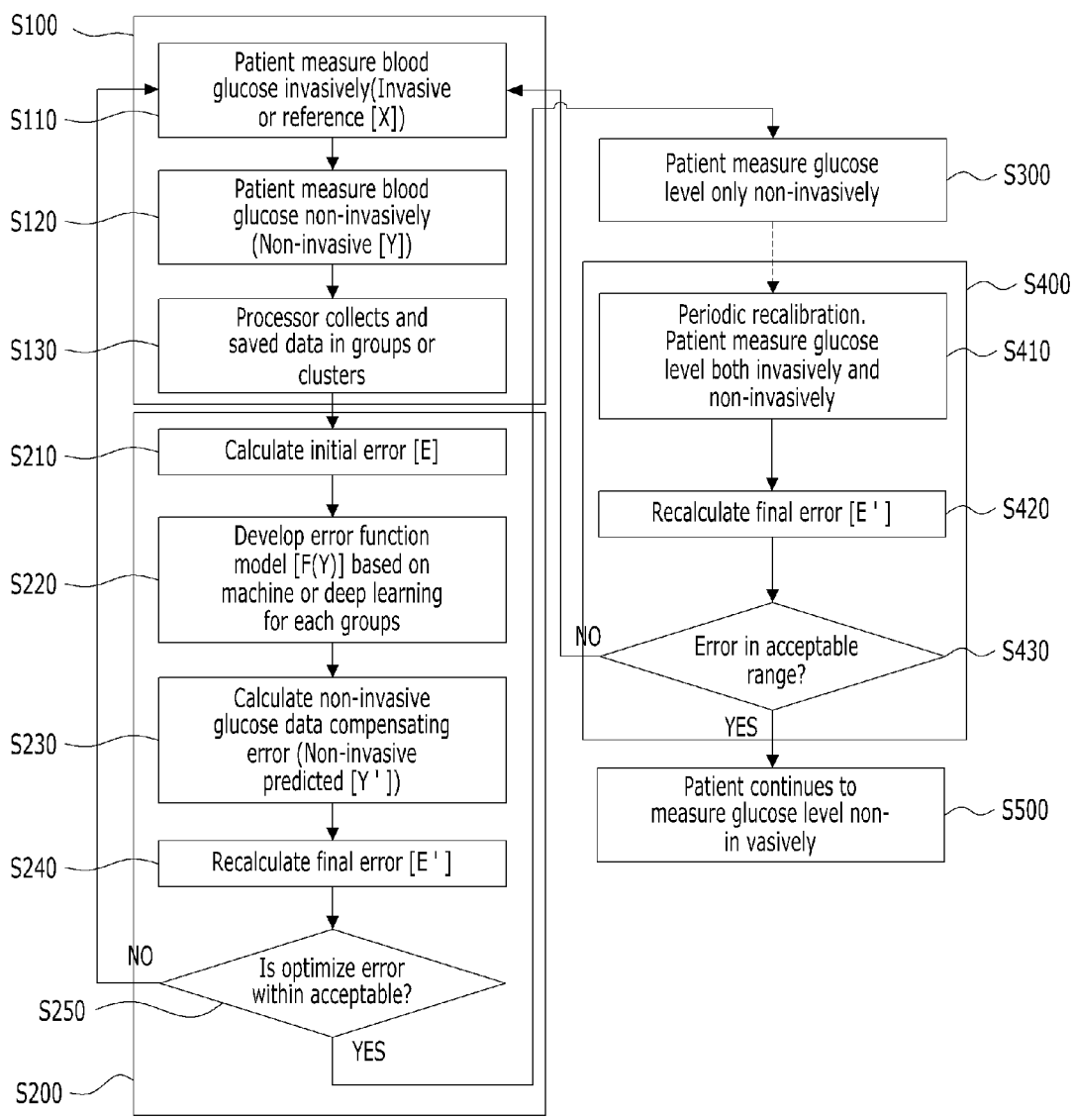

[FIG. 3]
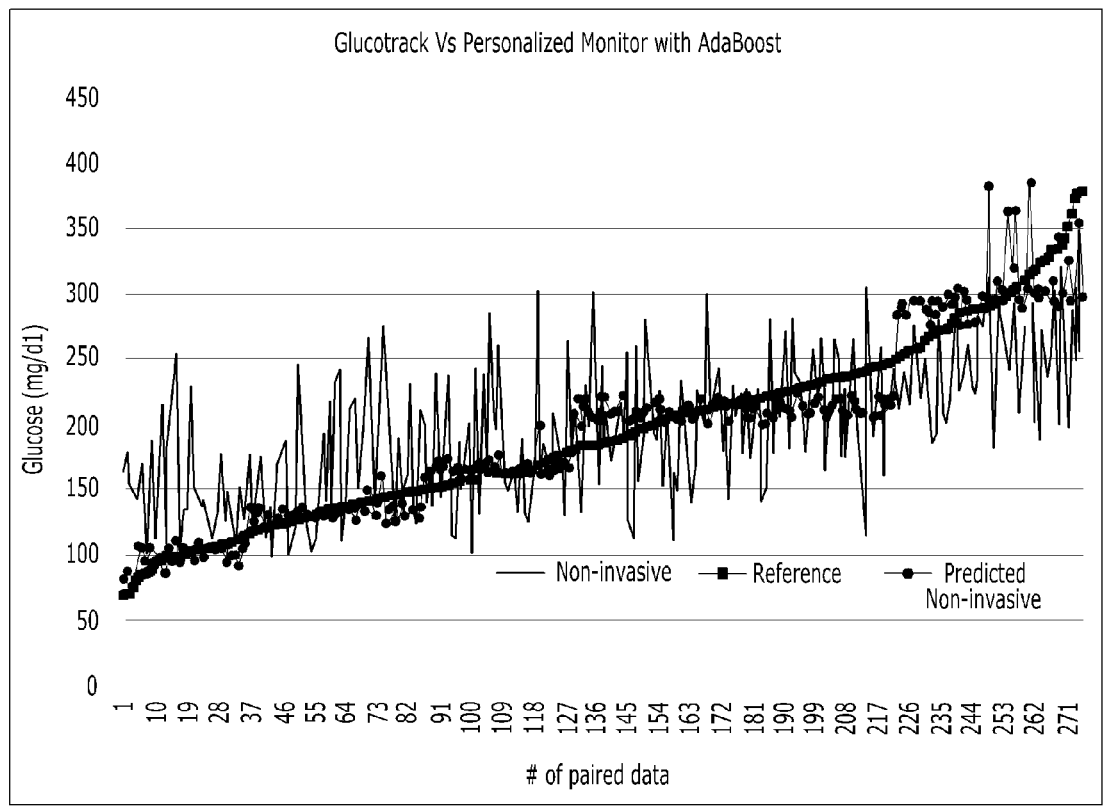

PERSONALIZED NON-INVASIVE BLOOD GLUCOSE MEASUREMENT DEVICE USING MACHINE LEARNING OR DEEP LEARNING AND METHOD USING THE MEASUREMENT DEVICE

CROSS-REFERENCE TO RELATED APPLICATIONS

This application claims the priority of Korean Patent Application No. 10-2019-0060012 filed on May 22, 2019, in the Korean Intellectual Property Office, the disclosure of which is incorporated herein by reference.

BACKGROUND

Field

The present disclosure relates to a personalized non-invasive blood glucose measurement device using machine learning or deep learning and a non-invasive blood glucose measurement method by the measurement device, and more particularly, to a personalized non-invasive blood glucose measurement device using machine learning or deep learning which when an invasive sensor or a non-invasive sensor initially measures a blood glucose of a patient, calculates an error of non-invasive measurement for an invasive blood glucose value by a processor unit, builds an error function model by an optimal machine or deep learning regressive analysis based on collected data, and then accurately calculates non-invasively blood glucose value using an error function model which is optimized for a personal through error compensation, and a non-invasive blood glucose measurement method by the measurement device.

Description of the Related Art

According to the World Health Organization (WHO), approximately 422 million people are suffering from the diabetes and approximately 1.6 million people died in 2014. The number of diabetics is increasing at an annual rate of 8.5%, and by 2030 more than one billion people are expected to suffer from this disease.

Over the last few decades, various non-invasive blood glucose devices have been developed using various non-invasive sensor technologies. Some of the devices are called CNOGA, Glucotrack, Glucowise, Omeaho B2, Pepex mTrio. A non-invasive blood glucose measurement technology used for these devices is an infrared ray spectroscopy, an ultrasonic wave, an electromagnetic wave, an impedance spectroscopy, a diffuse reflectance, a Raman spectroscopy, a thermal sensing etc, or combination of multiple sensors. Unfortunately, all devices have failed clinical trials which satisfy the requirements of food and drug administration (FDA).

Most researchers are focusing on improving an accuracy of the non-invasive sensors.

However, the accuracy of the non-invasive measurement may greatly vary depending on a skin color, a skin thickness, skin temperature, heredity, last food intake, recent physical activity and anxiety of a patient. Most researchers mainly focus on the improvement of the accuracy of the sensors, but have not completely solved the inaccuracy of the non-invasive blood glucose measurement due to within patient or in-between patients' variations.

Therefore, a personalized blood glucose monitoring device which is capable of providing a more accurate result is necessary.

RELATED ART DOCUMENT

Patent Document

Japanese Laid-Open No. 2009-039267 (published on Feb. 26, 2009).

SUMMARY

In accordance with the above-described necessity, an object of the present disclosure is to provide a personalized non-invasive blood glucose measurement device using machine learning or deep learning which when an invasive sensor and a non-invasive sensor initially measure a blood glucose of a patient, calculates an error of non-invasive measurement with respect of an invasive blood glucose value by a processor unit, builds an error function model by an optimal regressive analysis using machine or deep learning based on collected data, and then non-invasively accurately calculates the blood glucose with an error function model which is optimized for a personal through error compensation, and a non-invasive blood glucose measurement method by the measurement device.

In order to achieve the above-described object, a personalized non-invasive blood glucose measurement method according to the present disclosure includes: (a) collecting blood glucose value data of a patient by a processor unit both invasively and non-invasively; (b) determining an acceptable final error E' with the non-invasive blood glucose value data collected by the processor unit; ((c) non-invasively predicting a blood glucose value in accordance with a setting mode by a patient when the final error E' is determined, to measure a blood glucose value accurately, by the processor unit; (d) periodically determining whether the final error E' is calibrated by the processor unit; and (e) when it is not necessary to recalibrate in step (d), non-invasively predicting the blood glucose value in a range of the final error E' determined in step (b) to measure the blood glucose value, by the processor unit.

In order to achieve the above-described object, in the personalized non-invasive blood glucose measurement method according to the present disclosure, the step (a) includes: (a-1) receiving an invasive blood glucose value X from an invasive blood glucose measurement unit, by the processor unit; (a-2) receiving a non-invasive blood glucose value Y from a non-invasive blood glucose measurement unit, by the processor unit; and (a-3) collecting data by storing the invasive blood glucose value X between the invasive blood glucose value X and the non-invasive blood glucose value Y which are received by the processor unit in a memory in different groups or clusters based diabetes condition as per blood glucose ranges.

In order to achieve the above-described object, in the personalized non-invasive blood glucose measurement method according to the present disclosure, the step (b) includes: (b-1) calculating an initial error E by comparing the non-invasive blood glucose value Y with the invasive blood glucose value X which is a reference value by a comparator of the processor unit; (b-2) building an error function model by an error function model generating unit of the processor unit; (b-3) compensating an error in the non-invasive blood glucose value Y using the error function model to predict an expected non-invasive glucose value Y' which is close to the invasive blood glucose value X which is a reference value, by an error compensating unit of the processor unit; (b-4) calculating a final error E' by comparing the expected non-invasive blood glucose value Y' and the invasive blood glucose value X by the comparator; and (b-5) determining whether the final error E' is in a predetermined acceptable range by the processor unit to confirm the final error E' when the final error E' is in the acceptable range.

In order to achieve the above-described object, in the personalized non-invasive blood glucose measurement method according to the present disclosure, the step (b) further includes: (b-5') repeating steps after the step (a) by the processor unit when the final error E' is not in the acceptable range.

In order to achieve the above-described object, in the personalized non-invasive blood glucose measurement method according to the present disclosure, the step (d) includes: (d-1) newly collecting the expected non-invasive blood glucose value Y' and the invasive blood glucose value X by the processor unit; (d-2) recalculating a final error E' by comparing the expected non-invasive blood glucose value Y' and the invasive blood glucose value X collected in the step (d-1) by the comparator; and (d-3) repeating steps after the step (a) to calibrate the final error E' by the processor unit when as a result of redetermining whether the final error E' calculated in the step (d-2) is in a predetermined acceptable range, the final error is not in the acceptable range.

In order to achieve the above-described object, in the personalized non-invasive blood glucose measurement method according to the present disclosure, the step (d-3) further includes: (d-3') continuously applying the corresponding final error E' to measure a non-invasive blood glucose value of the patient by the processor unit when as a result of redetermining whether the final error E' calculated in the step (d-2) is in a predetermined acceptable range, the final error is in the acceptable range.

In order to achieve the above-described object, in the personalized non-invasive blood glucose measurement method according to the present disclosure, in the step (b-2), the error function model generating unit reflects internal variation (food intake, physical activities, stress, and anxiety) of the patient and external variation (genetic nature, a skin color, a skin thickness, and a sensor accuracy) of the patient which are sources of variation of the non-invasive blood glucose measurement to learn the variation and then builds the error function model.

Desirably, a personalized non-invasive blood glucose measurement device using machine learning or deep learning according to the present disclosure includes: a non-invasive blood glucose measurement unit which measures a blood glucose by a non-invasive sensor; an invasive blood glucose measurement unit which measures a blood glucose by an invasive sensor; a processor unit which collects an invasive blood glucose value and a non-invasive blood glucose value measured by the invasive blood glucose measurement unit and the non-invasive blood glucose measurement unit to calculate an error and generates a personalized error function model through the learning using machine learning or deep learning to compensate an error to calculate a predicted non-invasive blood glucose value; a mode selecting unit which selects a mode to output any one of the invasive blood glucose value, the non-invasive glucose value, and the predicted non-invasive blood glucose value; and a display unit which displays any one of a selection mode by the mode selecting unit, patient information, time and date information, the invasive blood glucose value, the non-invasive blood glucose value, and the predicted non-invasive blood glucose value.

In the personalized non-invasive blood glucose measurement device using machine learning or deep learning according to the present disclosure, the processor unit includes: a non-invasive data receiving unit which receives a non-invasive blood glucose value Y measured by the non-invasive blood glucose measurement unit; an invasive data receiving unit which receives an invasive blood glucose value X measured by the invasive blood glucose measurement unit; a comparator which calculates an initial error E by comparing the non-invasive blood glucose value Y with the invasive blood glucose value X which is a reference value or calculates a final error E' by comparing a predicted non-invasive blood glucose value Y' with the invasive blood glucose value X; an error function model generating unit which builds an error function model using the initial error E after reflecting internal variation (food intake, physical activities, stress, and anxiety) of the patient and external variation (genetic nature, a skin color, a skin thickness, and a sensor accuracy) of the patient in the information of the patient to learn the variation; and an error compensating unit which compensates an error in the non-invasive blood glucose value Y using the error function model to predict the expected non-invasive glucose value Y' which is close to the invasive blood glucose value X which is a reference value.

According to the personalized non-invasive blood glucose measurement device using machine learning or deep learning and the non-invasive blood glucose measurement method by the measurement device according to the present disclosure, a blood glucose of a patient is measured by an invasive sensor and a non-invasive sensor and an error function model which corrects a blood glucose value measured by the non-invasive sensor with respect to a blood glucose value invasively measured is built to provide an accurate personalized non-invasive blood glucose value to patients who need to invasively measure a blood glucose every day.

BRIEF DESCRIPTION OF THE DRAWINGS

The above and other aspects, features and other advantages of the present disclosure will be more clearly understood from the following detailed description taken in conjunction with the accompanying drawings, in which:

FIG. 1 is a structure diagram of a personalized non-invasive blood glucose measurement device using machine learning or deep learning according to the present disclosure;

FIG. 2 is a flowchart of a personalized non-invasive blood glucose measurement method according to the present disclosure; and FIG. 3 is a graphic view of a test result of invasive, non-invasive, and non-invasive predicted blood glucose values.

DETAILED DESCRIPTION OF THE PREFERRED EMBODIMENT

Those skilled in the art may make various modifications to the present invention and the present invention may have various embodiments thereof, and thus specific embodiments will be described in detail with reference to the drawings. However, it should be understood that the invention is not limited to the specific embodiments, but includes all changes, equivalents, or alternatives which are included in the spirit and technical scope of the present invention. In the description of respective drawings, similar reference numerals designate similar elements.

Terms such as first, second, A, or B may be used to describe various components but the components are not limited by the above terms. The above terms are used only to discriminate one component from the other component. For example, without departing from the scope of the present invention, a first component may be referred to as a second component, and similarly, a second component may be referred to as a first component. A term of and/or includes combination of a plurality of related elements or any one of the plurality of related elements.

It should be understood that, when it is described that an element is "coupled" or "connected" to another element, the element may be directly coupled or directly connected to the other element or coupled or connected to the other element through a third element. In contrast, when it is described that an element is "directly coupled" or "directly connected" to another element, it should be understood that no element is not present there between.

Terms used in the present application are used only to describe a specific exemplary embodiment, but are not intended to limit the present invention. A singular form may include a plural form if there is no clearly opposite meaning in the context. In the present application, it should be understood that term "include" or "have" indicates that a feature, a number, a step, an operation, a component, a part or the combination those of described in the specification is present, but do not exclude a possibility of presence or addition of one or more other features, numbers, steps, operations, components, parts or combinations, in advance.

If it is not contrarily defined, all terms used herein including technological or scientific terms have the same meaning as those generally understood by a person with ordinary skill in the art. Terms defined in generally used dictionary shall be construed that they have meanings matching those in the context of a related art, and shall not be construed in ideal or excessively formal meanings unless they are clearly defined in the present application.

In the specification and the claim, unless explicitly described to the contrary, the word "comprise" and variations such as "comprises" or "comprising", will be understood to imply the inclusion of stated elements but not the exclusion of any other elements.

Hereinafter, a personalized non-invasive blood glucose measurement device using machine learning or deep learning according to the present disclosure and a non-invasive blood glucose measurement method by the measurement device will be described with reference to the accompanying drawings.

First, a personalized non-invasive blood glucose measurement device using machine learning or deep learning according to the present disclosure includes a non-invasive blood glucose measurement unit 100, an invasive blood glucose measurement unit 200, a processor unit 300, a mode selecting unit 400, and a display unit 500.

The processor unit 300 includes a non-invasive data receiving unit 310, an invasive data receiving unit 320, a memory (not illustrated), a comparator 330, an error function model generating unit 340, an error compensating unit 350, and an output unit 360.

The non-invasive blood glucose measurement unit 100 and the invasive blood glucose measurement unit 200 may non-invasively and invasively measure blood glucose values, respectively, as illustrated in FIG. 1.

The non-invasive blood glucose measurement unit 100 may be any non-invasive sensor for example an IR sensor based on a near-infrared technique and the invasive blood glucose measurement unit 200 may be an invasive sensor, but are not limited thereto and various invasive sensors and non-invasive sensors may be used.

The processor unit 300 collects an invasive blood glucose value and a non-invasive blood glucose value measured by the non-invasive blood glucose measurement unit 100 and the invasive blood glucose measurement unit 200 to calculate an error and generates an error function model to compensate the error, thereby predicting a non-invasive blood glucose value.

More specifically, the processor unit 300 includes the non-invasive data receiving unit 310, the invasive data receiving unit 320, the memory (not illustrated), the comparator 330, the error function model generating unit 340, the error compensating unit 350, and the output unit 360. The non-invasive data receiving unit 310 receives a non-invasive blood glucose value measured by the non-invasive blood glucose measurement unit 100 and the invasive data receiving unit 320 receives an invasive blood glucose value measured by the invasive blood glucose measurement unit 200 to store the blood glucose values in the memory.

When the non-invasive data receiving unit 310 and the invasive data receiving unit 320 receive the blood glucose values, the memory stores an invasive blood glucose value which is invasively measured and a non-invasive blood glucose value which is non-invasively measured, but, desirably, stores the invasive blood glucose value as a reference value.

The comparator 330 compares the non-invasive blood glucose value with the invasive blood glucose which is a reference value to calculate an initial error as illustrated in FIG. 1.

In the meantime, the blood glucose values measured by the non-invasive blood glucose measurement unit 100 and the invasive blood glucose measurement unit 200 are converted into a digital signal by an A/D converter to be transmitted to the comparator 330.

The error function model generating unit 340 in which a software program is stored builds an "error function model" based on collected data by applying a regressive model to reduce a sum of square error (SSE).

The error function model is built using various regressive models using machine learning or other artificial intelligence methods. For example, these machine or deep models are random forest, support vector, multilayer perceptron, decision tree, adaptive boosting (AdaBoost), k-nearest neighbors (KNN) etc. The machine or deep learning models are built after dividing the invasive and non-invasive blood glucose paired data into six groups or clusters based on invasive value. These six groups or clusters are based on diabetes patient conditions and blood glucose range as shown in Table for an example. These groups divided based on blood glucose range for a patient condition as Hypoglycemia, No Diabetes, Pre diabetes, Hyperglycemia, Highly Diabetes and Critically diabetes. The machine or deep learning models are built for each six groups separately. Each group machine or deep learning models predict non-invasive value Y' separately. The invention is not limited to six groups but it is a representative number. The main point is invasive and non-invasive paired data are divided into different groups or cluster before making machine or deep learning models.

| Random mean blood glucose (mg/dL) | Patient condition |
|---|---|
| 50 to 80 | Hypoglycemia |
| 81 to 115 | No diabetes |
| 116 to 150 | Pre diabetes |
| 151 to 180 | Hyperglycemia |
| 181 to 250 | Highly diabetes |
| >250 | Critically diabetes |

The error compensating unit 350 compensates an error in the non-invasive blood glucose value using the "error function model" to predict an expected non-invasive glucose value Y' which is close to the invasive blood glucose value.

The output unit 360 outputs an invasive blood glucose value, non-invasive blood glucose value, or corrected non-invasive blood glucose value which is input in accordance with a mode selection.

The mode selecting unit 400 allows the patient to select an output signal of the output unit as mentioned above.

The display unit 500 is connected to the output unit 360 to display the measured blood glucose value as a numerical value together with a selected mode, a patient name, a date, and a time.

As another embodiment, a non-invasive blood glucose measurement method by the personalized non-invasive blood glucose measurement device using machine learning or deep learning with the above-described configuration will be described.

First, parameters used in the personalized non-invasive blood glucose measurement device using machine learning or deep learning according to the present disclosure are as follows:

TABLE 1

| Parameter | Definition |
|---|---|
| X | Invasive (reference) glucose value |
| Y | Non-invasive glucose value |
| Y' | Non-invasive predicted (or corrected) glucose value |
| E | Initial error in non-invasive glucose value |
| E' | Final error in non-invasive predicted glucose value |
| F(Y) | Error function model developed by machine or deep learning models |

First, the personalized non-invasive blood glucose measurement device using machine learning or deep learning according to the present disclosure performs a step of collecting data (S100).

More specifically, a patient performs a step of measuring an invasive blood glucose value X using the invasive blood glucose measurement unit 200 (S110).

Further, the patient performs a step of measuring a non-invasive blood glucose value Y with the non-invasive blood glucose measurement unit 100 (S120).

Next, the non-invasive data receiving unit 310 and the invasive data receiving unit 320 of the processor unit 300 perform a step of collecting data by receiving the invasive blood glucose value X and the non-invasive blood glucose value Y to store the values in the memory (S130). The paired data are saved after dividing them into six groups or clusters based on invasive value (S130). These six groups or clusters are based on diabetes patient conditions and blood glucose range as shown in Table for an example. These groups divided based on blood glucose range for a patient condition as Hypoglycemia, No Diabetes, Pre diabetes, Hyperglycemia, Highly Diabetes and Critically diabetes. The invention is not limited to six groups but it is a representative number. The main point is invasive and non-invasive paired data are divided into different groups or cluster before making machine or deep learning models.

In this case, desirably, the processor unit 300 may store the received invasive blood glucose value X and the non-invasive blood glucose value Y in the memory with the invasive blood glucose value X as a reference value.

In the meantime, before the step S130, the A/D converter may further perform a step of converting the invasive blood glucose value X and the non-invasive blood glucose value Y which are analog values into digital values.

Even though not illustrated in FIG. 2, the step S130 may be sufficiently inferred through the contents illustrated in FIG. 1.

After the step S100, the processor unit 300 performs a step of calculating an acceptable final error E' (S200).

To more specifically describe the step S200, the comparator 330 of the processor unit 300 performs a step of comparing the non-invasive blood glucose value Y with the invasive blood glucose value which is a reference value to calculate an initial error E using Equation 1 (S210).

$$E = \frac{100 \times (Y - X)}{X} \qquad \text{[Equation 1]}$$

Next, the error function model generating unit 340 may perform a step of building an "error function model F(Y)" which reduces a sum of square error (SSE) between the non-invasive blood glucose value Y and the invasive blood glucose value X based on data collected by applying a machine learning or deep learning model (S220). For example, these machine or deep models are random forest, support vector, multilayer perceptron, decision tree, adaptive boosting (AdaBoost), k-nearest neighbors (KNN) etc. The machine or deep learning models are trained for each six groups separately as divided in step (S130). Each group machine or deep learning models predict non-invasive value Y' separately.

In this case, in order to ensure a universal usage of the non-invasive blood glucose measurement device, the error function model generating unit 340 performs the learning to build the error function model F(Y) in consideration of internal variation (food intake, a physical activity, stress, anxiety, and the like) of the patient and external variation (a genetic nature, a skin color, a skin thickness, a sensor accuracy, and the like) of the patient which are sources of variation of the non-invasive blood glucose measurement.

Specifically, in the present disclosure, the error function model generating unit 340 is trained in accordance with a skin color, a skin thickness, an amount of food intakes, a physical activity, stress, and other psychological patterns of the patient to be personalized.

The error compensating unit 350 performs a step of compensating an error in the non-invasive blood glucose value Y using the "error function model" to predict an expected non-invasive glucose value Y' which is close to the invasive blood glucose value X (S230).

Again, the comparator 330 of the processor unit 300 performs a step of recalculating a final error E' of the expected non-invasive blood glucose value Y' and the invasive blood glucose value X (S240).

The final error E' is recalculated by the following Equation 2.

$$E' = \frac{100 \times (Y' - X)}{X} \quad \text{[Equation 2]}$$

The final error E' is reduced to a value between −32% and 22% as compared with the initial error between −221% and 61% as summarized in the following Table 2 on a data set. This proves the improvement of the accuracy of the personalized non-invasive blood glucose measurement device using machine learning or deep learning according to the present disclosure. The mean average relative difference MARD reduced from 23.4% to 7.3%.

TABLE 2

| Parameter | Unit | Minimum | Maximum | Mean |
|---|---|---|---|---|
| X | mg/dl | 65 | 402 | 192 |
| Y' | mg/dl | 77 | 385 | 194 |
| E | % | −221 | 61 | 23.4 |
| E' | % | −32 | 22 | 7.3 |

The processor unit 300 determines whether the final error E' is in a predetermined acceptable range. When the final error E' is in the acceptable range, the processor unit 300 confirms the final error E' and when the final error E' is not in the acceptable range, repeats the processes after the step S100 of collecting the data (S250).

As described above, when the final error E' in the acceptable range is determined, the personalized non-invasive blood glucose measurement device using machine learning or deep learning according to the present disclosure performs a step of only non-invasively measuring a blood glucose value in accordance with a setting by a patient (S300).

More specifically, when the patient is notified to use only non-invasive measurement, the personalized non-invasive blood glucose measurement device using machine learning or deep learning according to the present disclosure may set the mode selecting unit 400 to allow only the non-invasive measurement.

Since the final error E' may vary depending on the internal variation (food intake, a physical activity, a stress, an anxiety, and the like) of the patient or the external variation (a genetic nature, a skin color, a skin thickness, a sensor accuracy, and the like) of the patient, the processor unit 300 performs a step of periodically recalibrating the final error E' (S400).

More specifically, when the patient measures the expected non-invasive blood glucose value Y' and the invasive blood glucose value X by the non-invasive blood glucose measurement unit 100 and the invasive blood glucose measurement unit 200 periodically at every set period, that is, when the set period arrives, the processor unit 300 performs a step of collecting new data (S410).

The comparator 330 performs a step of recalculating the final error E' using the invasive blood glucose value X measured in step S410 and the expected non-invasive blood glucose value Y' (S420).

Further, the processor unit 300 redetermines whether the final error E' recalculated in step S420 is in a predetermined acceptable range (S430) and when the final error E' is in the acceptable range, the processor unit 300 performs a step of continuously applying the final error E' to measure the non-invasive blood glucose value of the patient (S500).

However, when the recalculated final error E' is not in the acceptable range, processes after the step S100 of collecting data are repeatedly performed to readjust the personalized non-invasive blood glucose measurement device using machine learning or deep learning according to the present disclosure.

In the meantime, as illustrated in FIG. 3 which is a graphic view of a test result of invasive, non-invasive, and expected non-invasive blood glucose values, it is clearly confirmed that the non-invasive prediction curve follows the invasive blood glucose curve.

It will be appreciated that various exemplary embodiments of the present invention have been described herein for purposes of illustration, and that various modifications, changes, and substitutions may be made by those skilled in the art without departing from the scope and spirit of the present invention. Accordingly, the exemplary embodiments disclosed herein are intended to not limit but describe the technical spirit of the present invention and the scope of the technical spirit of the present invention is not restricted by the exemplary embodiments. The protective scope of the present disclosure should be construed based on the following claims, and all the technical concepts in the equivalent scope thereof should be construed as falling within the scope of the present disclosure.

What is claimed is:

1. A processor-implemented method for determining a personalized non-invasive blood glucose measurement, the method comprising:
   (a) using an invasive sensor to measuring invasive blood glucose value X of a patient;
   (b) using a non-invasive sensor to measure non-invasive blood glucose value Y of the patient;
   (c) collecting data by receiving the invasive blood glucose value X and the non-invasive blood glucose value Y, storing the values in a memory and saving the data from steps (a) and (b) in groups;
   (d) calculating an acceptable final error E' in the non-invasive blood glucose value by:
      (d-1) calculating an initial error E in the non-invasive glucose value by comparing the non-invasive blood glucose value Y with the invasive blood glucose value X:
      (d-2) developing an error function model F(Y) for each of the groups based on a machine learning or deep learning;
      (d-3) calculating a non-invasive glucose compensating error using the error function model F(Y) to predict an expected non-invasive blood glucose value Y' that is close in value to that of the invasive blood glucose value X;
      (d-4) calculating the final error E' of the expected non-invasive blood glucose value Y' and the invasive blood glucose value X; and
      (d-5) determining whether the final error E' is within an acceptable range;
   (e) in response to the final error E' being in the acceptable range, using the non-invasive sensor to measure non-invasive blood glucose value Y of the patient;
   (f) periodically recalibrating the final error E' by:
      (f-1) collecting new data by measuring glucose level both invasively and non-invasively;
      (f-2) recalculating the final error E' using the invasive blood glucose value X measured in step (f-1) and the expected non-invasive blood glucose value Y' (S420); and
      (f-3) determining whether the final error E' is within the acceptable range;

(f-4) in response to the final error E' not being in the acceptable range, repeating steps (a)-(f); and (g) in response to the final error E' being in the acceptable range, predicting the blood glucose level of the patient non-invasively.

2. The method according to claim 1, wherein in the step (d-2), the error function model F(Y) is built by using internal variation and external variation of the patient, the internal variation and external variation being sources of variation of the non-invasive blood glucose measurement.

3. The method according to claim 1,
wherein the error function model F(Y) uses:
internal variation of the patient comprising at least one of food intake, a physical activity, stress, anxiety, or any combination thereof; and
external variation of the patient comprising at least one of a genetic nature, a skin color, a skin thickness, a sensor accuracy, or any combination thereof.

4. The method according to claim 1, wherein the error function model F(Y) for each of the groups based on machine learning or deep learning model reduces a sum of square error (SSE) between the non-invasive blood glucose value Y and the invasive blood glucose value X.

5. A personalized non-invasive blood glucose measurement device comprising:
an invasive sensor to measure invasive blood glucose value X of a patient;
a non-invasive sensor to measure non-invasive blood glucose value Y of the patient;
a memory:
a processor configured to:
collect data by receiving the invasive blood glucose value X and the non-invasive blood glucose value Y, store the values in the memory and saving the data from the invasive sensor and the non-invasive sensor in groups;
calculate an acceptable final error E' in the non-invasive blood glucose value by:
calculating an initial error E in the non-invasive glucose value by comparing the non-invasive blood glucose value Y with the invasive blood glucose value X;
developing an error function model F(Y) for each of the groups based on a machine learning or deep learning;
calculating a non-invasive glucose compensating error using the error function model F(Y) to predict an expected non-invasive blood glucose value Y' that is close in value to that of the invasive blood glucose value X;
calculating the final error E' of the expected non-invasive blood glucose value Y' and the invasive blood glucose value X; and
determining whether the final error E' is within an acceptable range;
wherein, in response to the final error E' being in the acceptable range, using the non-invasive sensor to measure non-invasive blood glucose value Y of the patient;
wherein the processor is further configured to periodically recalibrating the final error E' by:
collecting new data by measuring glucose level both invasively and non-invasively;
recalculating the final error E' using the invasive blood glucose value X measured in step (f-1) and the expected non-invasive blood glucose value Y' (S420); and
determining whether the final error E' is within the acceptable range;
wherein, in response to the final error E' not being in the acceptable range, the processor is further configured to repeat the recalibration, and
wherein, in response to the final error E' being in the acceptable range, the processor is further configured to predict the blood glucose level of the patient non-invasively.

6. The personalized non-invasive blood glucose measurement device according to claim 5, wherein the error function model F(Y) uses internal variation and external variation of the patient, wherein the internal variation comprises at least one of food intake, physical activity, stress, anxiety, or any combination thereof.

7. The personalized non-invasive blood glucose measurement device according to claim 6, wherein the external variation of the patient comprises at least one of a genetic nature, a skin color, a skin thickness, a sensor accuracy, or any combination thereof.

8. The personalized non-invasive blood glucose measurement device according to claim 5, wherein the groups are determined based on a patient condition comprising one of hypoglyclemic, not diabetic, pre-diabetic, hyperglycemic, highly diabetic, and critically diabetic as determined by mean blood glucose values.

* * * * *